United States Patent [19]

Yahagi et al.

[11] Patent Number: 4,824,604
[45] Date of Patent: Apr. 25, 1989

[54] DETERGENT COMPOSITION

[75] Inventors: Kazuyuki Yahagi, Tokyo; Kaoru Tsujii, Wakayama; Hajime Hirota, Tokyo; Yoshihisa Matsumura, Wakayama, all of Japan

[73] Assignee: Kao Corporation, Tokyo, Japan

[21] Appl. No.: 51,329

[22] Filed: May 19, 1987

[30] Foreign Application Priority Data

May 26, 1986 [JP] Japan .................................. 61-120399
Sep. 17, 1986 [JP] Japan .................................. 61-217286
Sep. 17, 1986 [JP] Japan .................................. 61-217287

[51] Int. Cl.$^4$ .......................... C11D 1/37; C11D 1/94
[52] U.S. Cl. .................................... 252/546; 252/544;
252/545; 252/547; 252/549; 252/DIG. 14;
260/404; 562/567
[58] Field of Search .................... 260/404; 562/567;
252/527, 529, 546, 548, 545, 544, 547, 549,
DIG. 14

[56] References Cited

FOREIGN PATENT DOCUMENTS 577921 6/1959 Canada .
1813671 6/1970 Fed. Rep. of Germany .

Primary Examiner—A. Lionel Clingman
Assistant Examiner—Hoa Van Le
Attorney, Agent, or Firm—Oblon, Fisher, Spivak, McClelland & Maier

[57] ABSTRACT

Novel detergent composition comprises one or more of N-acyl-N-hydroxyalkylglycines of the general formula (I) or salts thereof:

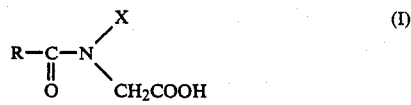

The composition has a very good resistance to hard water, low stimulativeness, and good detergency. It is thus suitably employed as shampoo for babies, kitchen detergent and the like.

6 Claims, 1 Drawing Sheet

DETERGENT COMPOSITION

BACKGROUND OF THE INVENTION

(1) Field of the Invention

This invention relates to detergent compositions which comprise specific types of N-acyl-N-hydroxyalkylglycines as a substrate and have good properties, and also to novel N-acyl-N-hydroxypropylglycines useful as the substrate for detergents.

(2) Description of the Prior Art

Detergents are required not only to have good detergent properties such as detergency and foaming power, but also to provide a low stimulus to the skin and the eye especially when they are used in direct contact with the skin as detergents for washing human bodies, e.g. shampoos, body shampoos and the like, detergents for tablewares and cooking utensils, and light detergents for wool.

These detergents contain surface active agents as a primary component. In most cases, anionic surface active agents are used for this purpose, including, for example, soaps (salts of fatty acids), linear alkylbenzenesulfonates (LAS), alkylsulfates (AS), polyoxyethylene alkyl ether sulfates (AES), alpha-olefinsulfonates (AOS), and the like. Although the anionic surface active agents exhibit high detergency, they are all stimulative to the skin and the mucous membrane of the eye, thus being not considered as the best surface active agent for use as a primary ingredient for the detergent. On the other hand, low stimulative surface active agents have been proposed including, for example, monoalkylphosphates, and N-acylamino acid salts such as N-acylglutamates, N-acyl-N-alkyl-beta-alanine salts, N-acyl-N-alkylglycine salts and the like. Although these salts are less stimulative, problems are involved in inherent detergent properties such as a hard water resistance, foaming and detergent properties and the like, economy and preparation.

With soaps (fatty acid salts), if divalent and higher valent metallic ions such as calcium ions are present, lime soap (scum) insoluble in water is formed. This is true of N-acylamino acid salts. The scum deposits on articles to be washed or a washtub at the time of washing and on a bath tub, a washing backet, tiles, the skin, the hair and the like at the time of bathing, thus causing the problems such as of the redeposition of dirt on the washings and the worsening of a bathing environment.

Accordingly, there is a demand for detergents which has a low stimulation, high detergency and a good hard water resistant and also for compounds exhibiting such characteristic properties as mentioned above.

SUMMARY OF THE INVENTION

Under these circumstances in the art, the present inventors made intensive studies to solve the above problems and, as a result, found that specific types of N-acyl-N-hydroxyalkylglycines used as a substrate can provide detergent compositions which have a low stimulation, high detergency, high foaming powder and a good hard water resistance. The present invention is accomplished based on the above finding.

More particularly, the present invention provides a detergent composition which comprises one or more of N-acyl-N-hydroxyalkylglycines of the general formula (I), or salts thereof

in which RCO represents a saturated or unsaturated fatty acid residue having from 8 to 18 carbon atoms, and X represents a hydroxyalkyl group having from 1 to 4 carbon atoms.

DETAILED DESCRIPTION OF THE INVENTION AND PREFERRED EMBODIMENTS

Figure 1:
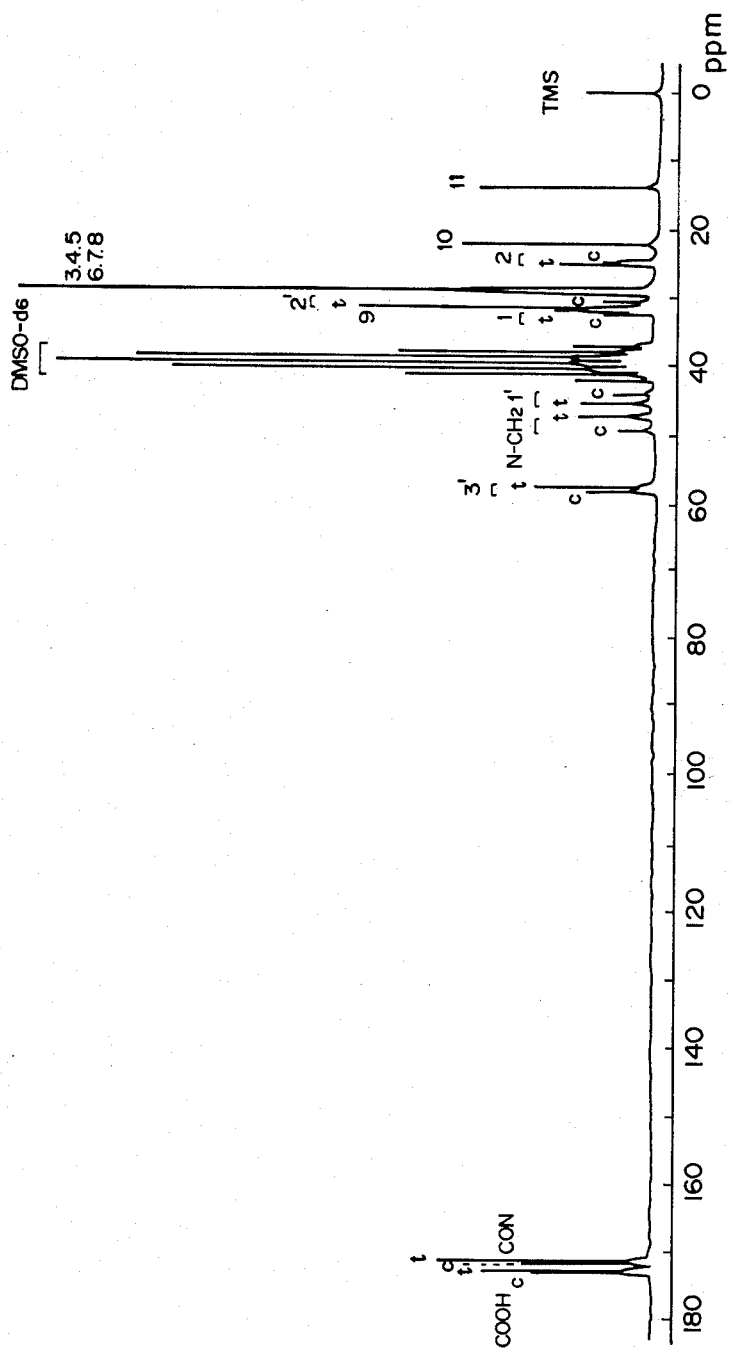
FIG. 1 is a chart showing a $^{13}$C-NMR of the N-lauroyl-N-(3-hydroxypropyl)glycine obtained in Example 1.

Preferable examples of the group, RCO, in the general formula (I) include lauroyl, myristoyl, palmitoyl, stearoyl, oleoyl, isostearoyl, coconut oil fatty acid residues and the like. The groups represented by X include, for example, hydroxylmethyl, 2-hydroxyethyl, 3-hydroxypropyl, 2-hydroxypropyl, 4-hydroxybutyl, and the like. The salts of the N-acyl-N-hydroxyalkylglycines (I) include, for example, salts with alkali metals such as sodium, potassium and the like, alkaline earth metals such as calcium, magnesium and the like, ammonium, alkanolamines having a hydroxyalkyl group having from 1 to 3 carbon atoms, alkyl-substituted ammonium having from 1 to 3 carbon atoms, and basic amino acids such as lysine, arginine and the like.

Of the compounds of the general formula (I), the compounds of the following general formulae (II) and (III) are novel and, in fact, preferable

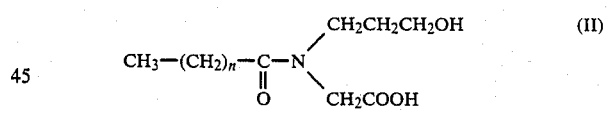

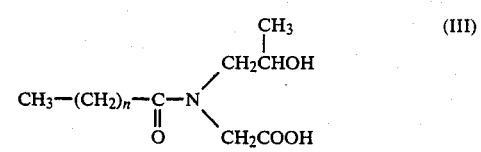

in which n is an integer of from 8 to 16.

Accordingly, the present invention has also as its object the provision of N-acyl-N-hydroxylpropylglycine compounds of the general formulae (II) and (III) and salts thereof.

Of the compounds of the formulae (II) and (III), preferable examples include compounds whose $CH_3(CH_2)_n$—CO— group is lauroyl, myristoyl, palmitoyl, or stearoyl. Preferable salts are sodium salts and triethanolamine salts.

The N-acyl-N-hydroxyalkylglycines (I) or salts thereof are prepared, for example according to the following reaction formula

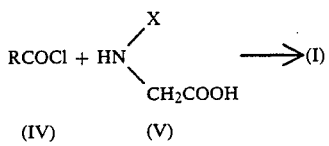

(IV)    (V)

in which R and X have, respectively, the same meanings as defined before. More particularly, a fatty acid chloride (IV) and an N-hyroxyalkylglycine (V) are reacted in the presence of a base, thereby obtaining compound (I).

The reaction is carried out, for example, by dropping fatty acid chloride (V) into an aqueous solution of N-hydroxyalkylglycine (V) at room temperature while adjusting the pH of 10 to 12 by the use of an aqueous potassium hydroxide solution.

The fatty acid chloride (IV) can be obtained by acting phosphorus trichloride on a corresponding fatty acid. The N-hydroxyalkylglycine (V) can be obtained by a suitable amount of an aqueous solution of sodium monochloroacetate into an aqueous alkanolamine solution and heating the mixture under reflux for several hours [J. Amer. Chem. Soc., 78, 172 (1956)].

When the compound of the general formula (III) is repeatedly heated and dehydrated, a cyclic compound of the following general formula (VI) is obtained

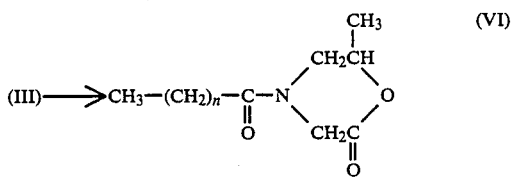

in which n has the same meaning as defined before.

Upon heating in the presence of water and an alkali, the cyclic-compound is readily ring-opened into compound (III) or its salts of the invention.

The amount of the N-acyl-N-hydroxyalkylglycine (I) or its salt in the detergent composition of the invention may vary depending upon the type of detergent and the types of acyl group and salt. If used as a main ingredient for the detergent, the glycine or salt thereof is preferably in the range of from 5 to 50 wt% (hereinafter referred to simply as %) for liquid detergents, and from 15 to 80% for paste detergents. In either case, the detergents are added with water so as to be 100% totally and are adjusted in pH to from 4 to 10, preferably from 5.5 to 7.5 by means of a suitable acid or alkali. Alternatively, the present substance may be used as solid or powder products by mixing 50 to 99% of the substance with other appropriate excipients, if necessary.

The N-acyl-N-hydroxyalkylglycine (I) or its salt has the function of enhancing foaming of anionic or amphoteric surface active agents ordinarily used as a main detergent active ingredient when added at a ratio to the anionic or amphoteric surface active agent of 1/20 to 1/1. Examples of these anionic surface active agents include alkylsulfates, alkyl ether sulfates, alpha-olefinsulfonates, alkyl phosphates, and alkyl ether phosphate and sulfosuccinic ester surface active agents. Examples of the amphoteric surface active agents include imidazoline amphoteric surface active agents. Of these, sodium alkyl ether sulfates and imidazoline amphoteric surface active agents are most preferable. These anionic or amphoteric surface active agents are used in an amount of from 5 to 50% for liquid detergents, from 15 to 80% for paste detergents and from 50 to 99% for solid or powder products.

The detergent composition of the invention may comprise, aside from the N-acyl-N-hydroxyalkylglycine (I) or its salt, auxiliary detergent active ingredients ordinarily used in detergents within a range from 0 to 10% of auxiliary detergent active ingredients, not impeding the properties of the detergent composition. Examples of such ingredients include amphoteric surface active agents such as alkanolamides, N-acylamino acid salts, N-alkylamino acid salts, alkylamine oxides, betaines, sulfobetaines, hydroxysulfobetaines and the like of higher fatty acids. If necessary, perfumes, dyes, humectants, preservatives, antioxidants, thickeners, and medical agents such as dandruff removers, bactericides, antiphologistics, vitamines and the like.

The mechanism of improvinf the hard water resistance, foming property and detergency with the N-acyl-N-hydroxyalkylglycine (I) or its salt, which is the substrate of the detergent composition of the invention, is assumed to result as follows.

In general, surface active agents can satisfactorily show the surface activity when used at temperatures higher than a melting point or a Krafft point of surface active agent-hydrated solids. Anionic surface active agents have generally so high Krafft points that limitation is placed on the conditions of use. Especially, when divalent or higher valent metallic ions such as calcium ions are present, the Krafft point sharply increases by occurrence of pair ion exchange of a surface active agent, the surface active agent precipitates in water within a practical temperature range as a hydrated solid such as a calcium salt of the surface active agent or deposits on an article being washed, thus losing the surface activity. Accordingly, for the improvement of the hard water resistance, the Krafft point of the calcium salt of a surface active agent has to be lowered to temperatures lower than a temperature of use. As a consequence, a good foaming property and good detergency in hard water is ensured.

Since known N-acylamino acid salts have peptide linkages

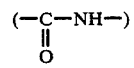

in the molecule, an intermolecular hydrogen bond is formed at the peptide linkage, resulting in an increase of the Krafft point.

On the other hand, N-acyl-N-alkylamino acid salts, e.g. an N-acylsarcosine salt and N-acyl-N-methyl-beta-alanine salt, in which the hydrogen atom of the peptide linkage is substituted with an alkyl group with the intermolecular hydrogen bonding ability being lost, are lower in the Krafft point. However, when divalent metallic ions such as calcium ions are present, 1 mole of the calcium ion associates with 2 moles of the surface active agent, thereby apparently forming a diacyl product. These products become so hydrophobic in nature that they cannot dissolve in water in a micellar form and aggregate with one another to form a scum, thus not acting as a detergent.

The N-acyl-N-hydroxyalkylglycines of the present invention are introduced at the site of the peptide linkage with an N-hydroxyalkyl substituent which will produce a great steric hindrance. As a result, the crystallinity of the hydrated solid of the surface active agent lowers with a drastic reduction of the Krafft point. In addition, if the surface active agent forms divalent metallic salts, such as a calcium salt, it dissolves in a micellar form because of the impartment of hydrophilicity with the hydroxyl group, showing satisfactorily the surface activity in hard water. This is considered as the reason why a good foaming property and high detergency are obtained.

According to the invention, there is obtained a detergent which has a very good resistance to hard water, a low stimulativeness, and good detergency. Accordingly, it is suitably employed as a detergent for the hair and skin for babies, kitchen detergents for housewives who are susceptible to chapping on the hand, and daily shampoos for humans who wash the hair every day. Moreover, the detergent is suitable as a low stimulative shampoo for barber and beauty parlor service workers who have to contact the shampoo over a long time.

The efficacy continues when applied not only to city water, but also a variety of hard waters such as underground water, spa water, and sea water.

The compounds of the formulae (II) and (III) or their salts have better surface activity, low stimulativeness and a good hard water resistance. If these compounds (II) and (III) are used as an additive for other types of surface active agents, a foaming effect in hard water is enhanced. Needless to say, these compounds can be used solely or in combination with other ingredients, similar to ordinary surface active agents, as a detergent for metal surface, antistatic agent, fiber treating agent, penetrating agent, emulsifier for emulsion polymerization and the like.

The invention is described in more detail by way of examples.

EXAMPLE 1

(1) 250 g of 3-amino-1-propanol and 500 g of water were charged into a 2 liter three-neck distillation flask, into which a mixture of 30 g of sodium monochloroacetate and 100 g of water was dropped in about 1 hour by the use of a dropping funnel while agitating at room temperature. After completion of the dropping, the reaction mixture was heated under reflux for further 3 hours at 90° to 100° C. to complete the reaction. Thereafter, 30 g of a 30% sodium hydroxide aqueous solution was added, followed by removal of the water and unreacted 3-amino-1-propanol under reduced pressure by distillation. 100 g of ethanol was added to the residue and agitated sufficiently and, after confirmation of the dissolution, 500 g of acetone was added. After cooling, the resultant product which was precipitated in the reactor was collected by filtration, followed by removal of the solvent by distillation under reduced pressure to obtain 40 g of the sodium salt of N-(3-hydroxypropyl)glycine.

IR (KBr) cm$^{-1}$: 3100–3500 ($\nu_{NH}$, $\nu_{OH}$), 2850–2950 ($\nu_{CH_2}$), 1600, 1400 ($\nu_{CO}$), 1060.

(2) 35 g of sodium N-(3-hydroxypropyl)glycine obtained in (1) and 100 g of water were charged into a 1 liter four-neck flask, into which 52 g of lauric acid chloride in about 1 hour by the use of a dropping funnel while agitating at room temperature, during which the pH of the reaction solution was maintained at 10 to 11 by dropping a 25% sodium hydroxide aqueous solution by the use of another dropping funnel. After completion of the dropping, agitation was continued until the pH of the reaction mixture did not change to complete the reaction. Hydrochloric acid was added to the reaction mixture to adjust the pH to about 3, followed by addition of ether and sufficient agitation to extract the reaction product. The ether phase was washed sufficiently with water and dehydrated with anhydrous sodium sulfate, followed by removal of the solvent by distillation. The resultant residue was dried under reduced pressure to obtain 55 g of a white solid of N-lauroyl-N-(3-hydroxypropyl)glycine.

M.P.: 55° C.

IR (KBr) cm$^{-1}$: 3200–3400 ($\nu_{OH}$), 2850–2950 ($\nu_{CH_2}$), 1735 ($\nu_{CO}$), 1625 ($\nu_{CO}$).

$^{13}$C-NMR (DMSO-d$_6$): FIG. 1.

Measured under complete $^1$H de-coupling conditions at about 30° C., with chemical shifts, δ, of $^{13}$C (ppm) indicated in Table 1 (TMS standards).

TABLE 1

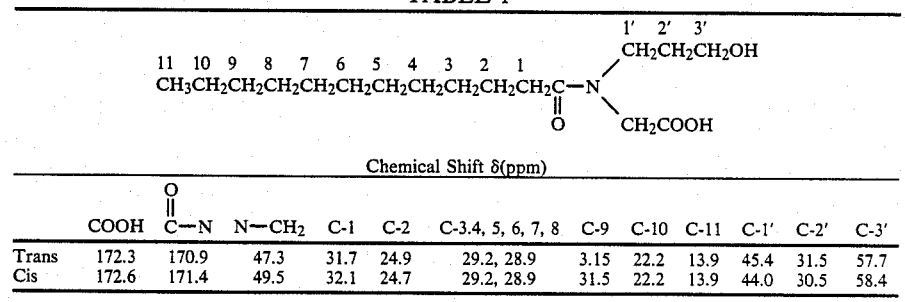

| | Chemical Shift δ(ppm) | | | | | | | | | | | | |
|---|---|---|---|---|---|---|---|---|---|---|---|---|---|
| | COOH | C—N (O) | N—CH$_2$ | C-1 | C-2 | C-3,4,5,6,7,8 | C-9 | C-10 | C-11 | C-1' | C-2' | C-3' |
| Trans | 172.3 | 170.9 | 47.3 | 31.7 | 24.9 | 29.2, 28.9 | 3.15 | 22.2 | 13.9 | 45.4 | 31.5 | 57.7 |
| Cis | 172.6 | 171.4 | 49.5 | 32.1 | 24.7 | 29.2, 28.9 | 31.5 | 22.2 | 13.9 | 44.0 | 30.5 | 58.4 |

EXAMPLE 2

Example 1 was repeated using instead of the lauric acid chloride, myristic acid chloride, palmitic acid chloride and stearic acid chloride, thereby obtaining N-myristoyl-N-(3-hydroxypropyl)glycine, N-palmitoyl-N-(3-hydroxypropyl)glycine and N-stearoyl-N-(3-hydroxypropyl)glycine, respectively.

EXAMPLE 3

20 g (0.0634 mole) of the N-lauroyl-N-(3-hydroxypropyl)glycine obtained in Example 1 and 20 ml of ethanol were charged into a 1 liter reactor equipped with an agitator and agitated at room temperature for uniform dissolution.

Thereafter, a solution of 2.536 g (0.0634 moles) of sodium hydroxide in 50 ml of ethanol was wholly dropped and agitated for neutralization of the N-lauroyl-N-(3-hydroxypropyl)glycine. 700 ml of acetone was added to the neutralized product, followed by cooling to 0° C. and allowing to stand thereby precipitating the sodium salt of N-lauroyl-N-(3-hydroxypropyl)glycine. The precipitate was removed by filtration and the solvent was distilled off under reduced pressure to obtain 15 g of the sodium salt of N-lauroyl-N-(3-hydroxypropyl)glycine.

IR (KBr) cm$^{-1}$: 3100–3400 ($\nu_{OH}$), 2850–2950 ($\nu_{CH_2}$), 1625 ($\nu_{CO}$), 1600, 1400 ($\nu_{CO}$).

EXAMPLE 4

15 g of the sodium salt of N-lauroyl-N-(3-hydroxypropyl)glycine obtained in Example 3 was dissolved in 200 g of ion-exchanged water, to which 5 g of calcium chloride was added and sufficiently agitated, followed by extraction with ether. In order to enhance the phase separation, 50 ml of methanol was dropped. The resultant extract with the ether was washed three times each 200 g of ion-exchanged water and dehydrated with anhydrous sodium sulfate. The sodium sulfate was removed by filtration and the solvent was distilled off under reduced pressure, followed by drying to obtain 5 g of a white solid of the calcium salt of N-lauroyl-N-(3-hydroxypropyl)glycine.

EXAMPLE 5

N-lauroyl-N-(3-hydroxypropyl)glycine was added to a predetermined amount of water, an equimolar amount of triethanolamine was added for neutralization, followed by sufficient agitation to obtain an aqueous solution of N-lauroyl-N-(3-hydroxypropyl)glycine triethanolamine salt.

EXAMPLE 6

(1) 375 g of monoisopropanolamine and 375 g of water were charged into a 2 liter four-neck flask and heated to 70° C. into which 350 g of a 33% monochloroacetic acid aqueous solution was dropped in 1 hour. Thereafter, the mixture was further agitated at 70° C. for 1 hour, into which 135 g of a 30% NaOH aqueous solution was dropped at 70° C. in 30 minutes, followed by further agitation at 70° C. for 30 minutes to complete the reaction. Thereafter, unreacted monoisopropynolamine was completely distilled off by heating under reduced pressure to obtain 212 g of the sodium salt of N-(2-hydroxypropyl)glycine.

This product contained sodium N-(2-hydroxypropyl)iminodiacetate, NaCl and NaOH. Because no problem was involved upon acylation, it was used as it is for subsequent acylation.

(2) 106 g of the sodium salt of N-(2-hydroxypropyl)glycine obtained in (1) and 130 g of water were charged into a 500 ml four-neck flask, into which 35 g of lauric acid chloride dropped by the use of a dropping funnel for 2 hours while agitating at 25° C. During this, a 30% NaOH aqueous solution was dropped by the use of another dropping funnel for pH control so as to maintain the pH at 10 to 11. After completion of the dropping, the system was agitated for 1 hour a pH of 10 to 11 to complete the reaction.

The resultant reaction system was adjusted in pH to about 2 by means of hydrochloric acid and extracted with ether to extract a reaction product. The ether phase was sufficiently washed with a saline solution, dehydrated with anhydrous sodium sulfate, and the ether was distilled off to obtain 23 g of a white solid of N-lauroyl-N-(2-hydroxypropyl)glycine. The thus obtained white solid was taken in a small amount, into which water was added and heated to obtain an emulsion which was acidic.

M.P.: 50° C.

IR (KBr): 2850 cm$^{-1}$ ($\nu_{CH_2}$), 2925 cm$^{-1}$ ($\nu_{CH_2}$), 1730 cm$^{-1}$ ($\nu_{C=O}$), 1630 cm$^{-1}$ ($\nu_{C=O}$).

The white solid was recrystallized three times with n-hexane (melted by heating to 60° C.), thereby obtaining a cyclic compound of the general formula (VI) (n=10).

M.P.: 62° C.

IR (KBr): 2850 cm$^{-1}$ ($\nu_{CH_2}$), 2930 cm$^{-1}$ ($\nu_{CH_2}$), 1735 cm$^{-1}$ ($\nu_{C=O}$), 1640 cm$^{-1}$ ($\nu_{C=O}$).

| | Elementary analysis: | |
| --- | --- | --- |
| | found | calculated |
| C | 68.40% | 68.69% |
| H | 10.55 | 10.44 |
| N | 4.74 | 4.71 |
| O | 16.58 | 16.16 |
| total | 100.27 | 100.00 |

EXAMPLE 7

Example 6 was repeated except that the lauric acid chloride was replaced by myristic acid chloride, palmitic acid chloride, and stearic acid chloride, thereby obtaining N-myristoyl-N-(2-hydroxypropyl)glycine, N-palmitoyl-N-(2-hydroxypropyl)glycine and N-stearoyl-N-(2-hydroxypropyl)glycine.

EXAMPLE 8

20 g (0.0634 moles) of the N-lauroyl-N-(2-hydroxypropyl)glycine obtained in Example 6 and 20 ml of ethanol were charged into a 1 liter reactor equipped with an agitator, followed by uniform dissolution by agitation at room temperature.

Thereafter, a solution of 2.536 g (0.0634 moles) of sodium hydroxide dissolved in 50 ml of ethanol was wholly dropped and well agitated for neutralization of the N-lauroyl-N-(2-hydroxypropyl)glycine. 700 ml of acetone was added to the neutralized product and cooled down to 0° C., followed by allowing to stand, thereby precipitating the sodium salt of N-lauroyl-N-(2-hydroxypropyl)glycine. The precipitate was removed by filtration and the solvent was distilled off under reduced pressure to obtain 15 g of the sodium salt of N-lauroyl-N-(2-hydroxypropyl)glycine.

EXAMPLE 9

15 g of the sodium salt of N-lauroyl-N-(2-hydroxypropyl)glycine obtained in Example 8 was dissolved in 200 g of ion-exchanged water, to which 5 g of calcium chloride was added and sufficiently agitated, followed by extraction with ether. 50 ml of methanol was dropped so as to facilitate the phase separation. The extract with the ether was washed three times each with 200 g of ion-exchanged water and dehydrated with anhydrous sodium sulfate. The sodium sulfate was removed by filtration and the solvent was distilled off under reduced pressure, followed by drying to obtain 5 g of the calcium salt of N-lauroyl-N-(2-hydroxypropyl)glycine as a white solid.

EXAMPLE 10

N-lauroyl-N-(2-hydroxypropyl)glycine was added to a predetermined amount of water, to which an equimolar amount of triethanolamine was added for neutralization, followed by sufficient agitation to obtain an aqueous solution of the triethanolamine salt of N-lauroyl-N-(2-hydroxypropyl)glycine.

TEST EXAMPLE 1

The compounds of the invention and the compounds for comparison were each added to ion-exchanged water or hard water in an amount of 1 wt% at room temperature so as to check their solubility. As a result, it was found that the inventive compounds exhibited good solubility even in hard water, with a good foaming property.

The solubility was evaluated according to the following standards.

○ : transparently dissolved, Δ: slightly opaque or in a dispersed state, x: not dissolved.

TABLE 2

| Compounds Tested | Solubility Ion exchanged water | Solubility Hard water (German hardness of 50°) |
|---|---|---|
| Inventive Compound | | |
| Sodium salt of N—lauroyl-N—(3-hydroxypropyl)glycine | ○ | ○ |
| Triethanolamine salt of N—lauroyl-N—(3-hydroxypropyl)glycine | ○ | ○ |
| Calcium salt of N—lauroyl-N—(3-hydroxypropyl)glycine | ○ | ○ |
| Sodium salt of N—lauroyl-N—(2-hydroxypropyl)glycine | ○ | ○ |
| Triethanolamine salt of N—lauroyl-N—(2-hydroxypropyl)glycine | ○ | ○ |
| Calcium salt of N—lauroyl-N—(2-hydroxypropyl)glycine | ○ | ○ |
| Comparative Compound | | |
| Sodium salt of N—lauroylglycine | ○ | X |
| Sodium salt of N—myristoylglycine | X | X |
| Sodium salt of N—stearoylglycine | X | X |
| Sodium salt of N—lauroylsarcosine | ○ | X |
| Sodium salt of N—lauroyl-N—ethylglycine | ○ | X |
| Sodium salt of N—lauroyl-N—n-propylglycine | ○ | Δ |
| Sodium salt of N—lauroly-N—n-butylglycine | ○ | Δ |
| Sodium salt of N—lauroyl-N—(2-hydroxyethyl)glycine | ○ | X |
| Sodium salt of N—lauroyl-β-alanine | X | X |
| Sodium salt of N—lauroyl-N—methyl-β-alanine | ○ | X |
| Sodium salt of N—lauroylglycil-glycine | X | X |
| Monosodium N—lauroyl-L-glutamate | X | X |
| Sodium salt of N—myristoylsarcosine | ○ | X |
| Sodium salt of N—palmitoylsarcosine | ○ | X |
| Sodium salt of N—stearoylsarcosine | Δ | X |

TEST EXAMPLE 2

Liquid detergents having formulations indicated in Table 3 (pH adjusted to 7 by the use of a small amount of citric acid) were prepared to evaluate a hard water resistance, foaming power and detergency.

Evaluation Methods (1) Foaming power test method (a) Each detergent composition was dissolved in hard water with a German hardness of 10°DH to obtain a 1% detergent aqueous solution, to which 0.2% of artificial dirt was added. The mixture was agitated by means of a flat propeller at 40° C. for 5 minutes in a cylinder under such conditions that the number of revolutions was 1000 r.p.m. and the revolution was reversed every 10 seconds. 30 seconds after completion of the agitation, the amount of foams were measured.

(b) Organoleptic evaluation using hair pieces

Hot water (40° C.) was contained in 25 g of hair pieces, to which 0.5 g of a detergent composition was applied, followed by crumpling for about 2 minutes to organoleptically evaluate the amount of foams.

Evaluation Standards

⊙ : good
○ : moderate
Δ: slightly poor
x: poor (2) Detergency test method (A) Artificially soiled cloth Artificial oily dirt was uniformly dispersed in a solvent, with which a wool muslin cloth contacted and dried to uniformly deposit the dirt thereon. This cloth was cut into 10 cm × 10 cm test pieces and tested.

(B) Washing conditions and method

A detergent composition was dissolved in hard water having a German hardness of 15° DH to make 1 liter of a 3% detergent aqueous solution. Five pieces of artificially soiled cloth and the aqueous solution were charged into a stainless beaker for a Targoto Meter, followed by agitation at 75 r.p.m. at 40° C. for 3 minutes. The cloth pieces were rinsed with running water and pressed with an iron for measurement of a reflectivity.

(C) Calculation of washing rate

The washing rate was calculated according to the following equation.

The reflectivities of the original piece of cloth prior to the washing and the soiled pieces prior to and after the washing at 460 m were measured by means of a self-recording colorimeter (available from Shimadzu Seisakusho K.K.) and the washing rate (%) was calculated from the following equation.

$$\text{Washing Rate (\%)} = \frac{\text{reflectivity after washing} - \text{reflectivity before washing}}{\text{reflectivity of original cloth} - \text{reflectivity before washing}} \times 100$$

The washing rate was determined as an average value of five measurements of the cloth pieces. The detergent aqueous solution prior to the washing had a pH of 7.0.

(3) Hard water resistance test method

Detergent compositions were prepared to have 0.5 wt% of an effective component and the water hardness was controlled at 10°, 20°, 40° and 100° DH. Each solution was placed in a transparent 100 ml glass container to visually observe the appearance at room temperature.

The evaluation was made according to the following standards.

○ : uniform and transparent as a whole without involving any singularities such as phase separation, precipitation and coagulation.

Δ: uniform as a whole but semi-transparent and cloudy.

x: not uniform with phase separation precipitation and coagulation being observed.

Results

The results are shown in Table 3.

TABLE 3

| Ingredient | Detergent for Comparison (1) | (2) | (3) | (4) | (5) | (6) | Detergent of Invention [1] | [2] | [3] |
|---|---|---|---|---|---|---|---|---|---|
| Sodium N—lauroylglycine | 20(%) | — | — | — | — | — | — | — | — |
| Sodium N—lauroylglycylglycine | — | 20 | — | — | — | — | — | — | — |
| Sodium N—lauroylsarcosine | — | — | 20 | — | — | — | — | — | — |
| Sodium N—lauroyl-N—ethylglycine | — | — | — | 20 | — | — | — | — | — |
| Sodium N—lauroyl-N—propylglycine | — | — | — | — | 20 | — | — | — | — |
| Sodium N—lauroyl-N—butylglycine | — | — | — | — | — | 20 | — | — | — |
| Sodium N—lauroyl-N—(2-hydroxyethyl)glycine | — | — | — | — | — | — | 20 | — | — |
| Sodium N—lauroyl-N—(2-hydroxypropyl)glycine | — | — | — | — | — | — | — | 20 | — |
| Sodium N—lauroyl-N—(3-hydroxypropyl)glycine | — | — | — | — | — | — | — | — | 20 |
| Water | 80 | 80 | 80 | 80 | 80 | 80 | 80 | 80 | 80 |
| Hard water resistance | | | | | | | | | |
| 10° DH | X | X | X | △ | ○ | ○ | ○ | ⊙ | ⊙ |
| 20° DH | X | X | X | X | △ | △ | △ | ⊙ | ⊙ |
| 40° DH | X | X | X | X | X | △ | X | ⊙ | ⊙ |
| 100° DH | X | X | X | X | X | X | X | ○ | ○ |
| Foaming powder (ml) | 0 | 0 | 0 | 0 | 51 | 44 | 79 | 101 | 116 |
| Detergent powder (%) | 15 | 17 | 22 | 31 | 43 | 48 | 52 | 55 | 56 |

TEST EXAMPLE 3

Liquid detergent compositions indicated in Table 4 were prepared and evaluated by the methods set forth in Test Example 2 to evaluate the characteristic properties. The results are shown in Table 4.

The detergents of the invention have a good hard water resistance, a good foaming property, and a good detergent property.

TABLE 4

| Ingredient | Detergent for Comparison (7) | (8) | (9) | Detergent of Invention [4] | [5] | [6] | [7] |
|---|---|---|---|---|---|---|---|
| Sodium polyoxyethylene(2.5) laurylether sulfate | 4.0% | 4.0 | 4.0 | 4.0 | 4.0 | 4.0 | 4.0 |
| Coconut oil fatty acid diethanolamide | 1.0 | 1.0 | 1.0 | 1.0 | 1.0 | 1.0 | 1.0 |
| Polyoxyethylene(80) hardened castor oil | 0.5 | 0.5 | 0.5 | 0.5 | 0.5 | 0.5 | 0.5 |
| Sodium N—lauroylsarcosine | 12.0 | — | — | — | — | — | — |
| Sodium N—lauroyl-L-glutamate | — | 12.0 | — | — | — | — | — |
| Sodium N—lauroyl-N—propylglycine | — | — | 12.0 | — | — | — | — |
| Sodium N—lauroyl-N—(2-hydroxyethyl)glycine | — | — | — | 12.0 | — | — | — |
| Sodium N—lauroyl-N—(2-hydroxypropyl)glycine | — | — | — | — | 12.0 | — | — |
| Sodium N—lauroyl-N—(3-hydroxypropyl)glycine | — | — | — | — | — | 12.0 | — |
| Sodium N—cocoyl-N—(3-hydroxypropyl)glycine | — | — | — | — | — | — | 12.0 |
| Phosphoric acid | suitable amount | → | → | → | → | → | → |
| Water | balance | → | → | → | → | → | → |
| pH (5% aqueous solution) | 6.0 | 6.0 | 6.0 | 6.0 | 6.0 | 6.0 | 6.0 |
| Hard water resistance | | | | | | | |
| 10° DH | △ | △ | ○ | ⊙ | ⊙ | ⊙ | ⊙ |
| 20° DH | X | X | ○ | ⊙ | ⊙ | ⊙ | ⊙ |
| 40° DH | X | X | X | ○ | ⊙ | ⊙ | ⊙ |
| 100° DH | X | X | X | △ | ○ | ○ | ○ |
| Foaming power (ml) | 103 | 92 | 88 | 145 | 151 | 155 | 120 |
| Detergent power (%) | 50 | 49 | 51 | 57 | 58 | 61 | 54 |
| Foaming property by organoleptic evaluation of a hair piece | ○ | △ | △ | ⊙ | ⊙ | ⊙ | ○ |

EXAMPLE 11

Bath Agent for Infants

A bath agent for infants having the following composition was obtained.

| (Composition) | |
|---|---|
| Sodium N—lauroyl-N—(3-hydroxypropyl)-glycine | 12.0(%) |
| Imidazoline amphoteric surface active agent* | 5.0 |
| Polyethylene glycol 6000 distearate | 2.0 |
| Irgasun DP-300 | 0.1 |
| Perfume, dye | small amount |
| Water | balance |

(pH adjusted to 6 with citric acid)

Total 100

*A mixture of $$C_{11}H_{23}CON\begin{matrix}CH_2CH_2OH\\ \diagdown\\ CH_2CH_2N\end{matrix}\begin{matrix}CH_2CH_2COOM\\ \diagdown\\ CH_2CH_2COOM\end{matrix}\text{ and}$$

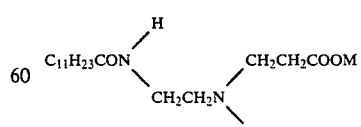

(in which M represents a mixture of Na and a hydrogen atom).

EXAMPLE 12

A champoo of the following composition was obtained.

| | |
|---|---|
| Triethanolamine salt of N—lauroyl-N—(3-hydroxypropyl)glycine | 10.0(%) |
| Sodium polyoxyethylene(2.5)lauryl ether sulfate | 5.0 |
| Diethanolamide laurate | 2.0 |
| Cationized cellulose | 0.3 |
| Perfume | 0.3 |
| Preservative | 0.1 |
| Dye | suitable amount |
| Citric acid | suitable amount |
| Water | balance |
| (pH adjusted to 6 with citric acid) | |
| Total | 100 |

EXAMPLE 13

A liquid detergent composition of the following composition was obtained.

| | |
|---|---|
| Sodium N—cocoyl-N—(3-hydroxypropyl)-glycine | 12.0(%) |
| Sodium N—cocoyl-N—(2-hydroxypropyl)-glycine | 8.0 |
| Ethanol | 2.0 |
| Propylene glycol | 3.0 |
| Perfume | 0.1 |
| Water | balance |
| (pH adjusted to 7 with citric acid) | |
| Total | 100 |

The detergent compositions of Examples 13-15 had good detergency and foaming property and a reduced degree of stimulation to the skin. Upon application to hard water, any scum was found to be formed, thus showing good properties.

EXAMPLE 14

Solid Detergent

| (Composition) | |
|---|---|
| (1) Sodium N—lauroyl-N—(3-hydroxypropyl)-glycine | 50.0(%) |
| (2) Sodium N—lauroyl-N—(2-hydroxyethyl)-glycine | 20.0 |
| (3) Diethanolamide coconut oil fatty acid salt | 5.0 |
| (4) Cetyl alcohol | 10.0 |
| (5) Glycerine | 5.0 |
| (6) Perfume, preservative | suitable amounts |
| (7) Water | balance |

(3)-(7) were mixed and emulsified under heating conditions, to which (1) and (2) were added and sufficiently kneaded by means of small-size rolls. The resultant paste was extruded through a small-size soap-making tester whose orifice was maintained at 40° to 50° C. The resultant detergent bar was molded using a foot-operated cutter to obtain a solid detergent.

This product was mild to the skin and gave abundant foams. Upon use in hard water, any scum did not form, thus showing good preperties.

EXAMPLE 15

A shampoo of the following formulation was obtained.

| | |
|---|---|
| Sodium polyoxyethylene(2.5)lauryl ether sulfate | 12.0(%) |
| Diethanolamide laurate | 3.0 |
| Sodium N—lauroyl-N—(2-hydroxyethyl)glycine | 5.0 |
| Polyoxyethylene(3) alkyl ether | 0.8 |
| Polyoxyethylene(120) hardened castor oil | 0.8 |
| Ethanol | 2.0 |
| Perfume | 0.3 |
| Preservative | 0.1 |
| Dye | suitable amount |
| Citric acid | suitable amount |
| Water | balance |
| Total | 100 |

EXAMPLE 16

A shampoo of the following composition was obtained.

| | |
|---|---|
| Imidazoline amphoteric surface active agent* | 10.0(%) |
| Sodium polyoxyethylene(2.5)lauryl ether sulfate | 5.0 |
| Triethanolamine salt of N—lauroyl-N—(3-hydroxypropyl)glycine | 5.0 |
| Diethanolamide coconut oil fatty acid | 2.0 |
| Perfume | 0.3 |
| Preservative | 0.1 |
| Dye | suitable amount |
| Citric acid | suitable amount |
| (amount sufficient to make a pH of 7) | |
| Water | balance |
| Total | 100 |

*Same as Example 11

What is claimed is:

1. A liquid detergent composition, comprising (1) a detergent base, (2) 5 to 50 wt.% of an anionic or amphoteric surface active agent, and (3) 5 to 50 wt.% of one or more N-acyl-N-hydroxyalkylglycines of the general formula (I) or salts thereof:

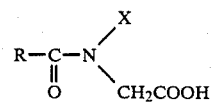

wherein:
RCO is a saturated fatty acid residue having from 8 to 18 carbon atoms; and
X is a 2-hydroxypropyl group or a 3-hydroxypropyl group.

2. The detergent composition of claim 1, wherein said RCO is a saturated fatty acid residue having 10, 12 or 14 carbon atoms.

3. A paste detergent composition, comprising (1) a detergent base, (2) 15 to 80 wt.% of an anionic or amphoteric active agent, and (3) 15 to 80 wt.% of one or more N-acyl-N-hydroxyalkylglycines of the general formula (I) or salts thereof:

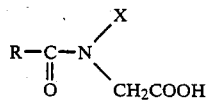

wherein:
RCO is a saturated fatty acid residue having from 8 to 18 carbon atoms; and
X is a 2-hydroxypropyl group or a 3-hydroxypropyl group.

4. The detergent composition of claim 3, wherein said RCO is a saturated fatty acid residue having 10, 12 or 14 carbon atoms.

5. A solid or powdered detergent composition, comprising (1) a detergent base, (2) 50 to 99 wt.% of an anionic of amphoteric surface active agent, and (3) 50 to 99 wt.% of one or more N-acyl-N-hydroxyalkylglycines of the general formula (I) or salts thereof:

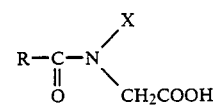

wherein:
RCO is a saturated fatty acid residue having from 8 to 18 carbon atoms; and
X is a 2-hydroxypropyl group or a 3-hydroxypropyl group.

6. The detergent composition of claim 5, wherein said RCO is a saturated fatty acid residue having 10, 12 or 14 carbon atoms.

* * * * *